(12) United States Patent
Fujita

(10) Patent No.: US 9,297,818 B2
(45) Date of Patent: Mar. 29, 2016

(54) SAMPLE ANALYZER

(71) Applicant: Sysmex Corporation, Kobe-shi, Hyogo (JP)

(72) Inventor: Kyozo Fujita, Akashi (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 14/799,029

(22) Filed: Jul. 14, 2015

(65) Prior Publication Data

US 2015/0316569 A1 Nov. 5, 2015

Related U.S. Application Data

(63) Continuation of application No. 11/894,941, filed on Aug. 22, 2007, now abandoned.

(30) Foreign Application Priority Data

Aug. 22, 2006 (JP) ................. 2006-225498
Aug. 22, 2006 (JP) ................. 2006-225499

(51) Int. Cl.
*G01N 35/00* (2006.01)
*G01N 35/10* (2006.01)

(52) U.S. Cl.
CPC ...... *G01N 35/00584* (2013.01); *G01N 35/0092* (2013.01); *G01N 35/00623* (2013.01); *G01N 35/00712* (2013.01); *G01N 35/00722* (2013.01); *G01N 35/10* (2013.01); *G01N 35/1002* (2013.01); *G01N 35/1004* (2013.01); *G01N 2035/0091* (2013.01)

(58) Field of Classification Search
CPC .................. G01N 35/00584; G01N 35/00623; G01N 35/00712; G01N 35/0092; G01N 2035/0091; G01N 35/00594; G01N 35/025; G01N 2030/8804; G01N 35/00613; G01N 35/00732; G01N 35/00871
See application file for complete search history.

(56) References Cited

U.S. PATENT DOCUMENTS

| | | | |
|---|---|---|---|
| 5,860,067 | A | 1/1999 | Onda et al. |
| 6,217,076 | B1 | 4/2001 | Howard et al. |
| 6,544,476 | B1 | 4/2003 | Mimura et al. |
| 6,611,275 | B1 | 8/2003 | Zey et al. |
| 2004/0138938 | A1 | 7/2004 | Quintus et al. |

(Continued)

FOREIGN PATENT DOCUMENTS

| | | | |
|---|---|---|---|
| EP | 0952452 | A1 | 10/1999 |
| EP | 1376138 | A2 | 1/2004 |

(Continued)

OTHER PUBLICATIONS

European Search Report for Corresponding European Patent Application No. EP 07016277 dated Jul. 6, 2009.
Office Action for corresponding U.S. Appl. No. 11/894,941 dated Mar. 2, 2010, 19 pages.

(Continued)

*Primary Examiner* — Shogo Sasaki
(74) *Attorney, Agent, or Firm* — Brinks Gilson & Lione

(57) ABSTRACT

A sample analyzer is disclosed that includes: a memory configured to store a record of maintenance already performed on the sample analyzer; a display; and a display control configured to control the display to display a first table which chronologically shows the record of maintenance already performed, wherein the first table is assigned a predetermined term, in the table the term is divided into a plurality of sections.

22 Claims, 8 Drawing Sheets

(56) References Cited

U.S. PATENT DOCUMENTS

| | | |
|---|---|---|
| 2005/0013736 A1 | 1/2005 | McKeever |
| 2005/0165582 A1 | 7/2005 | Tsung et al. |
| 2005/0175506 A1 | 8/2005 | Matsubara et al. |
| 2006/0024200 A1 | 2/2006 | Nishikiori et al. |

FOREIGN PATENT DOCUMENTS

| | | |
|---|---|---|
| JP | 02-150770 | 6/1990 |
| JP | 08-211064 | 8/1996 |
| JP | 09-211003 | 8/1997 |
| JP | 2002-181744 | 6/2002 |
| JP | 2008-292159 A | 12/2008 |

OTHER PUBLICATIONS

Office Action for corresponding U.S. Appl. No. 11/894,941 dated Oct. 26, 2010, 27 pages.
Office Action for corresponding U.S. Appl. No. 11/894,941 dated Mar. 30, 2011, 27 pages.
Office Action for corresponding U.S. Appl. No. 11/894,941 dated Aug. 2, 2011, 15 pages.
Office Action for corresponding U.S. Appl. No. 11/894,941 dated Oct. 24, 2012, 19 pages.
Office Action for corresponding U.S. Appl. No. 11/894,941 dated Feb. 8, 2013, 15 pages.
Office Action for corresponding U.S. Appl. No. 11/894,941 dated Jan. 14, 2014, 19 pages.
Office Action for corresponding U.S. Appl. No. 11/894,941 dated Jul. 11, 2014, 19 pages.

SAMPLE ANALYZER

RELATED APPLICATIONS

This application is a continuation of U.S. application Ser. No. 11/894,941 filed on Aug. 22, 2007, which claims priority under 35 U.S.C. §119 to Japanese Patent Application No. 2006-225498 filed Aug. 22, 2006 and Japanese Patent Application No. 2006-225499 filed Aug. 22, 2006, the entire contents of which are hereby incorporated by reference.

FIELD OF THE INVENTION

The present invention relates to a sample analyzer (hereinafter referred to simply as analyzer). More specifically, the present invention relates to an analyzer for displaying maintenance history or plan. In the specification, "analyzer" not only includes a device for analyzing samples such as urine and blood, but also includes a pre-processing device for analysis of smear processing device and the like.

BACKGROUND OF THE INVENTION

In a sample analyzer for analyzing samples such as urine and blood, maintenance of the apparatus is carried out according to a set plan (plan containing content and timing of maintenance) to mainly maintain a predetermined analytical precision. In the case of a blood coagulation measurement device, maintenance items include "pipette cleaning", "sample tube discarding" of discarding used cuvette (sample tube) accommodated in a discarding container and emptying the container, "fluid discharging process" of used cleaning fluid, etc., "reagent condensation removal" of removing condensation attached to the reagent container, and the like. The maintenance includes items which are to be carried out on a regular basis, and items which are carried out on an irregular basis such as replacement of consumable goods, pressure adjustment of air pressure source used in suction and dispensing of samples and reagents, and the like.

The maintenance includes items which are carried out by user or service person with the operation of the apparatus in a stopped state such as "sample tube discarding" and "reagent condensation removal", and items which require the apparatus to be operating such as "pipette cleaning". In the latter case, cases where the replacement task itself is performed by hand, but where the apparatus must be operated for replacement, such as the case in "pipette replacement", are also included. Specifically, in "pipette replacement", operations of moving the pipette to a replacement position, and returning the pipette to the original position after the replacement task by hand is completed are necessary. Japanese Laid-Open Patent Publication No. 2-150770 discloses an automatic analyzer that measures the number of operating times and the operating time of a mechanism section, stores the measured operating mechanism section by time, determines, from the stored content, whether or not it is in a period of time suited for maintenance operation such as period of time in which the analyzer is not used, and issues a maintenance start signal to perform the maintenance operation when determined as being in the period of time suited for maintenance operation.

Conventionally, such maintenance recording is carried out by the user writing the items performed only by hand and the items performed by operating the apparatus on a paper (maintenance record field written or attached to an apparatus manual or a copy of the same is often used). Japanese Laid-Open Patent Publication No. 9-211003 and Japanese Laid-Open Patent Publication No. 2002-181744 disclose an analyzer that stores the date the maintenance task was implemented and displays the date on the display section.

The maintenance recording paper is often attached to the manual, but in the conventional recording method, the chances of looking at the manual lowers as one gets familiarized with the operation of the apparatus, and thus may forget to record. The operation of the analyzer and the analyzing task are performed using a computer such as a personal computer, and the implementation of the maintenance involving the operation of the apparatus is also performed by instruction from an input means of the computer. In this case, the user instructs the implementation of the maintenance to the computer, and after checking the completion of the maintenance, the user must record the maintenance recording on the recording paper, which is a troublesome task. Furthermore, the recording paper is often not at hand when the user performing the analyzing task attempts to check the maintenance history, and thus the checking task becomes inconvenient.

In the automatic analyzer disclosed in Japanese Laid-Open Patent Publication No. 9-211003 and Japanese Laid-Open Patent Publication No. 2002-181744, since only the most recent date of when maintenance was implemented is merely displayed when displaying the maintenance recording, the user is only able to check at one time the most recent implementation date on the screen even for the maintenance task that is frequently (e.g., every day, every week) carried out, and thus cannot check at one time a plurality of maintenance implemented dates. Although it is desired that the person implementing the maintenance is also recorded in the maintenance history in terms of maintenance management, the user must input the person implementing the maintenance by hand in order to record the person implementing the maintenance in the automatic analyzer disclosed in Japanese Laid-Open Patent Publication No. 9-211003, whereby it is a burden on the user to input the person implementing the maintenance for every maintenance task, and furthermore, the user might forget to input.

SUMMARY OF THE INVENTION

The scope of the present invention is defined solely by the appended claims, and is not affected to any degree by the statements within this summary. A first sample analyzer embodying features of the present invention comprises: a memory configured to store a record of maintenance already performed on the sample analyzer; a display; and a display control configured to control the display to display a first table which chronologically shows the record of maintenance already performed, wherein the first table is assigned a predetermined term, in the table the term is divided into a plurality of sections.

A second sample analyzer embodying features of the present invention comprises: a memory configured to store a record of maintenance to be performed on the sample analyzer; a display; and a display control configured to control the display to display a first table which chronologically shows the record of maintenance to be performed, wherein the first table is assigned a predetermined term, in the table the term is divided into a plurality of sections.

A third sample analyzer embodying features of the present invention comprises: an analyzing mechanism configured to execute an analyzing operation for analyzing a sample and a maintenance operation; a memory configured to store a record of maintenance of the sample analyzer; an input section configured to instruct the maintenance operation of the analyzing mechanism; a display; a maintenance history displaying section configured to control the display so as to display a table which chronologically shows a maintenance history, the table being assigned a predetermined term, in the table the term being divided into a plurality of sections; a maintenance operation executor configured to control the analyzing mechanism so as to execute the maintenance operation when instruction to execute the maintenance operation is made from the input section; a record updater configured to control the memory to store a record of the maintenance executed by the maintenance operation executing section; and a display updater configured to update the maintenance history displayed on the display when the maintenance operation is executed.

A fourth sample analyzer embodying features of the present invention comprises: an analyzing mechanism configured to execute an analyzing operation for analyzing a sample and an operation involved in a maintenance task; a memory configured to store a record of maintenance of the sample analyzer; an input section configured to instruct the operation involved in the maintenance task of the analyzing mechanism; a display; a maintenance history displaying section configured to control the display so as to display a table which chronologically shows a maintenance history, the table being assigned a predetermined term, in the table the term being divided into a plurality of sections; an executor configured to control the analyzing mechanism to execute the operation involved in the maintenance task when accepting instruction to execute the operation involved in the maintenance task from the input section; a record updater configured to control the memory to store a record of the maintenance when the operation involved in the maintenance task is executed by the executor; and a display updater configured to update the maintenance history displayed on the display when the operation involved in the maintenance task is executed.

A fifth sample analyzer embodying features of the present invention comprises: an analyzing mechanism configured to execute an analyzing operation for analyzing a sample and a maintenance operation; a memory configured to store a record of maintenance of the sample analyzer; an input section configured to accept input from a user; a login section configured to authenticate the user based on user information input to the input section, and determining whether or not to permit the login of the user; a maintenance operation executor configured to control the analyzing mechanism to execute the maintenance operation when accepting instruction to execute the maintenance operation from the input section; and a record updater configured to control the memory to store information on the user who is logging in and the record of maintenance in association with each other when the maintenance operation is executed.

A sixth sample analyzer embodying features of the present invention comprises: an analyzing mechanism configured to execute an analyzing operation for analyzing a sample and a maintenance operation; a memory configured to store a record of maintenance of the sample analyzer; an input section configured to accept input from a user; a display; an instruction figures display section configured to display a plurality of instruction figures for respectively instructing a plurality of maintenance operations on the display; a maintenance operation executor configured to control the analyzing mechanism to execute the maintenance operation corresponding to the instruction figure when an input selecting the instruction figure is provided from the user to the input section; and a record updater configured to control the memory to store the record of maintenance executed by the maintenance operation executor.

DESCRIPTION OF THE PREFERRED EMBODIMENTS

The embodiments of an analyzer of the present invention will now be described based on the drawings.

Figure 1:
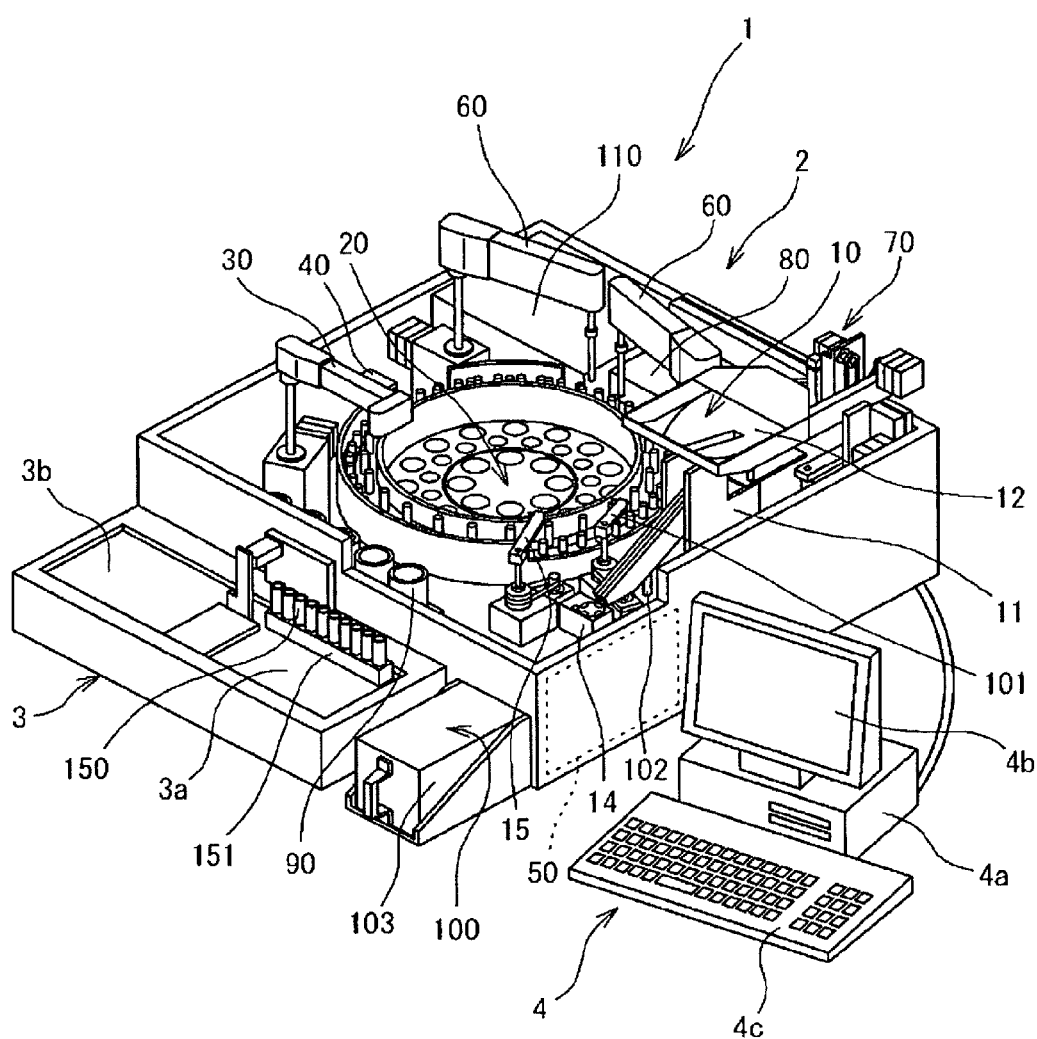
FIG. 1 is a perspective explanatory view showing the overall configuration of one embodiment of an analyzer of the present invention.
Figure 2:
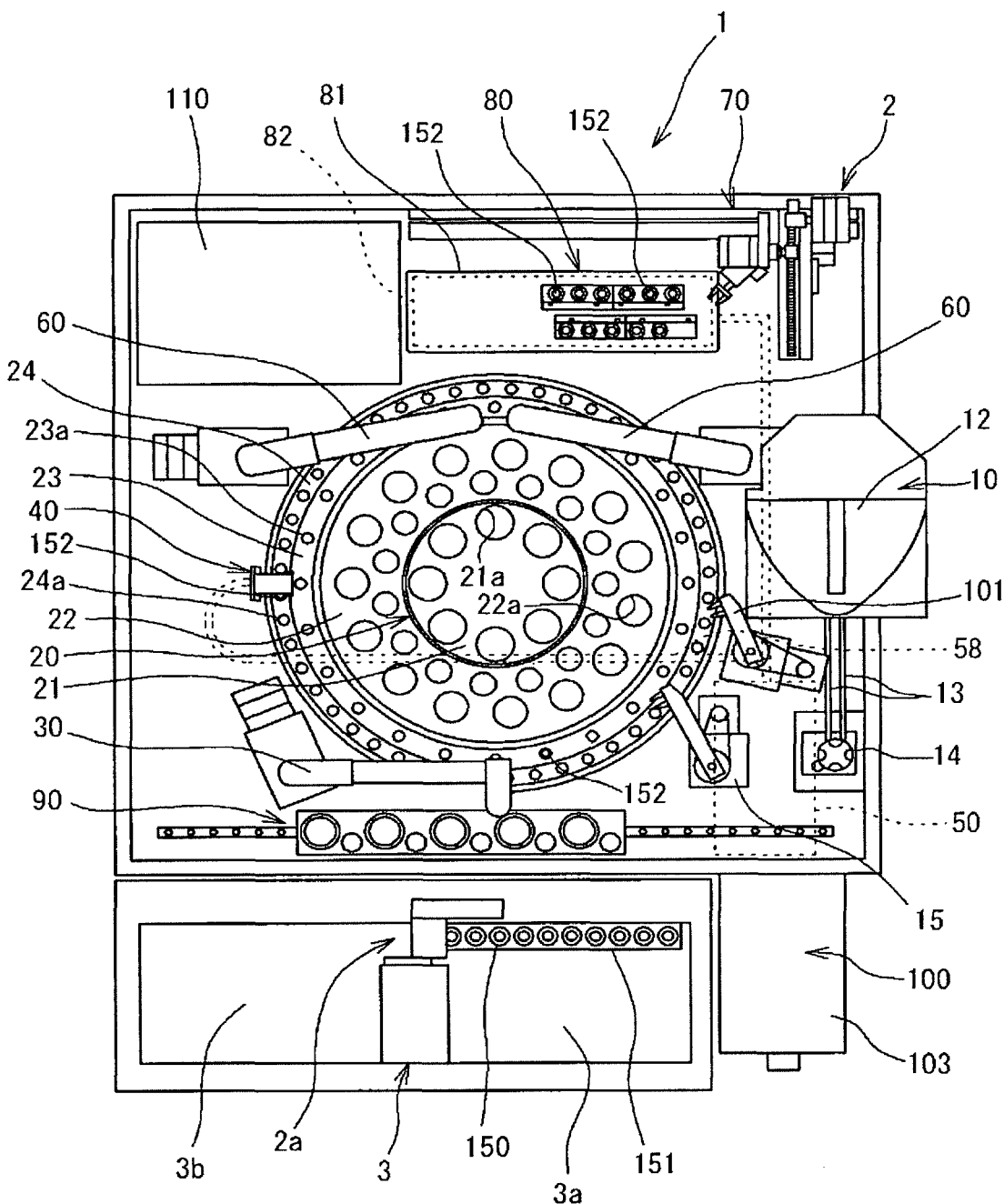
FIG. 2 is a plan explanatory view showing a measurement device and a conveying section in the analyzer shown in FIG. 1.
Figure 3:
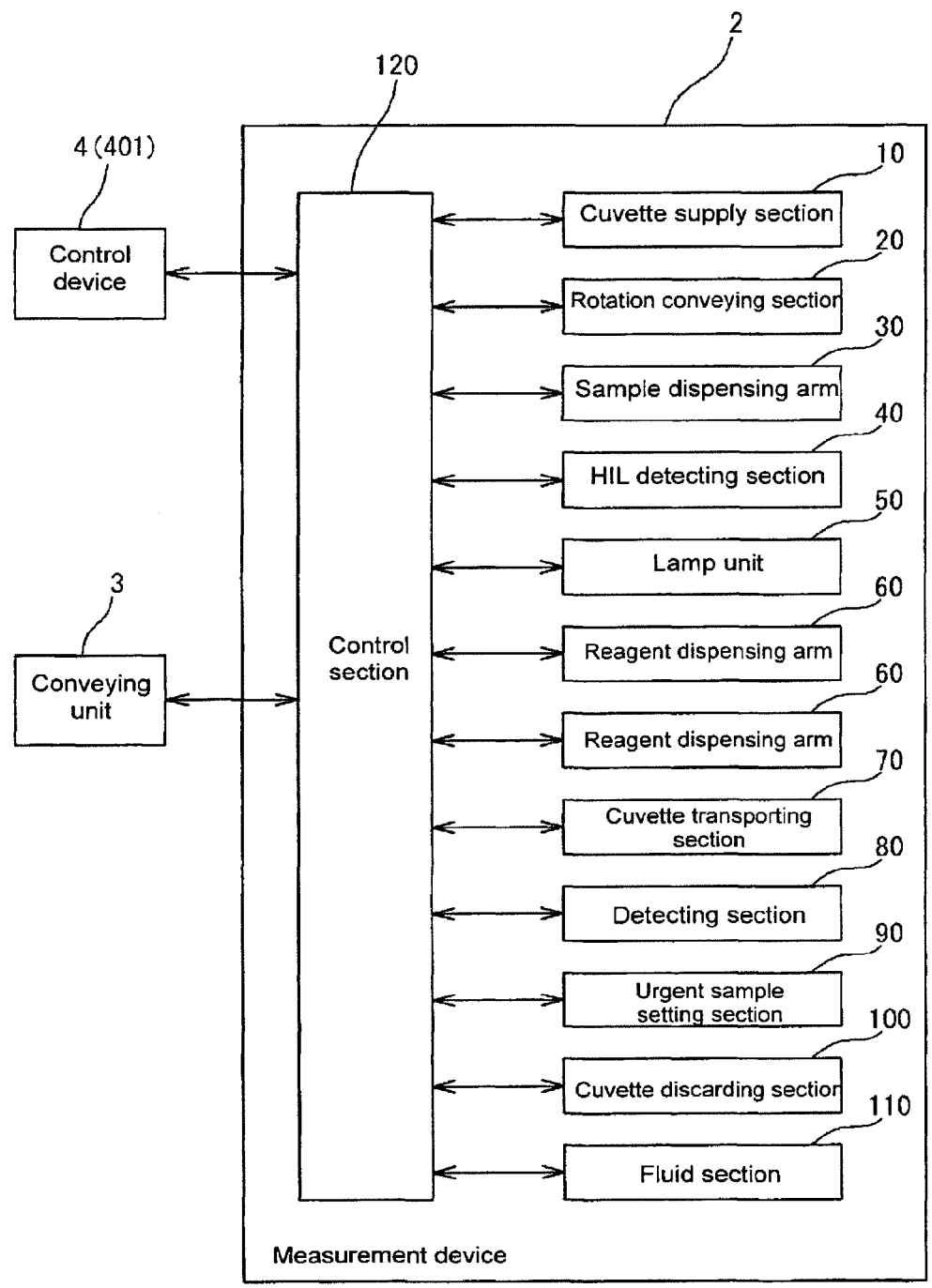
FIG. 3 is a block diagram showing a configuration of the measurement device in the analyzer shown in FIG. 1.
Figure 4:
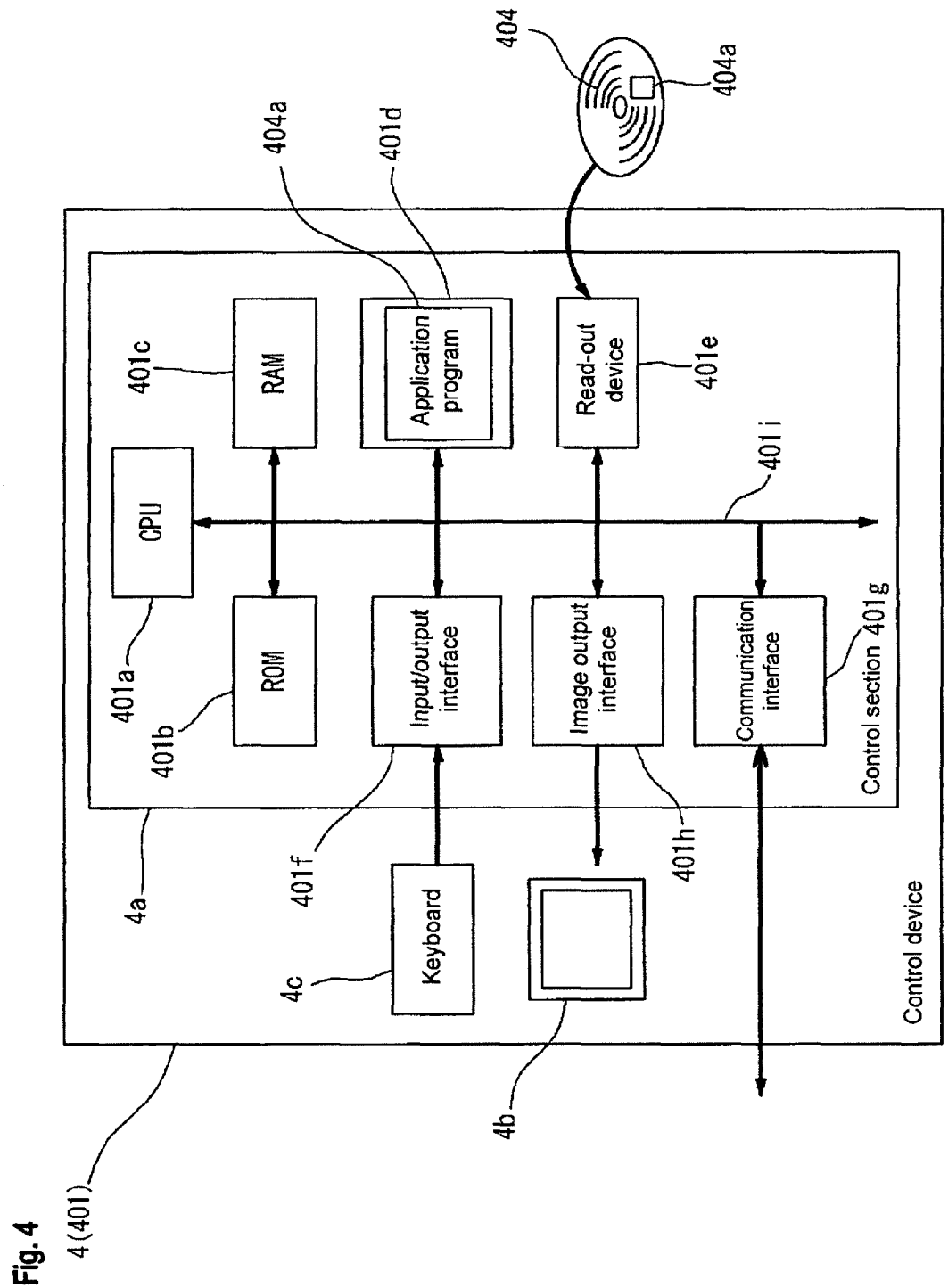
FIG. 4 is a block diagram of a control device in the analyzer shown in FIG. 1.

FIG. 1 is a perspective explanatory view showing the overall configuration of one embodiment of an analyzer of the present invention, FIG. 2 is a plane explanatory view showing a measurement device and a conveying section in the analyzer shown in FIG. 1, and FIG. 3 is a block diagram showing a configuration of the measurement device in the analyzer shown in FIG. 1. FIG. 4 is a block diagram of a control device in the analyzer shown in FIG. 1.

Overall Configuration of Analyzer

The overall configuration of the analyzer 1 according to the present embodiment will be described first. The analyzer 1 according to one embodiment of the present invention is an apparatus for optically measuring and analyzing the amount and extent of activity of a specific substance related to coagulation and fibrinolytic functions of the blood, where plasma is used for the blood sample. In the analyzer 1, optical measurement (main measurement) is performed using coagulation time method, synthetic substrate method, and immunoturbidmetric method. The coagulation time method used in the present embodiment is a measurement method of detecting the coagulating process of the sample as change in transmitted light. The measurement items include PT (prothrombin time), APTT (activated partial thromboplastin time), Fbg (Fibrinogen content), and the like. The measurement items of the synthetic substrate method include ATIII etc., and the measurement items of the immunoturbidmetric method include D dimer, FDP etc.

As shown in FIG. 1, the analyzer 1 is mainly configured by a measurement unit including a measurement device 2, a conveying unit 3 arranged on the front face side of the measurement device 2, and a control section 120 (see FIG. 3) for performing operation control of each mechanism in the measurement device 2 and the conveying unit 3; and a control device 4 serving as a data processing unit electrically connected to the measurement device 2. In the present embodiment, the conveying unit 3 and the measurement device 2 are integrated and form one part of the analyzer 1, but the conveying unit 3 may be a separate body from the analyzer 1. For instance, in a large-scale system including a plurality of analyzers, a mode in which a plurality of analyzers is connected to a large conveyance line may be adopted without arranging the conveying unit in each analyzer.

The control device 4 consists of personal computer 401 (PC) and the like, and includes a control section 4a, a display section 4b, and a keyboard 4c. The control section 4a has a function of performing operation control of the measurement device 2 and the conveying unit 3, as well as analyzing optical information of the sample obtained in the measurement device 2. The control section 4a consists of CPU, ROM, RAM, and the like. The display section 4b is arranged to display the result of analysis obtained in the control section 4a and to display maintenance history of the analyzer 1, as hereinafter described.

The control device 4 functions as an operating section of the user, creates a command from the operation instruction provided from the user through the keyboard 4c, and transmits the command to the control section of the measurement unit to enable the measurement unit to perform the operation such as start of analysis. Similar to the control section 4a, the control section of the measurement unit consists of CPU, ROM, RAM, and the like, and controls each mechanism in the measurement device 2 and the conveying unit 3 according to the command transmitted from the control device 4. The control section of the measurement unit also transmits the measurement data obtained in the measurement device 2 to the control device 4.

The configuration of the control device 4 will now be described. As shown in FIG. 4, the control section 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by bus 401i.

The CPU 401a can execute computer programs stored in the ROM 401b and the computer programs loaded in the RAM 401c. The computer 401 serves as the control device 4 when the CPU 401a executes the application program 404a, as hereinafter described. The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read the computer programs recorded on the ROM 401b and the hard disc 401d. The RAM 401c is used as a work region of the CPU 401a when executing the computer programs. The hard disc 401d is installed with various computer programs to be executed by the CPU 401a such as operating system and application program, as well as data used in executing the computer program. The application program 404a for calculating presence or concentration of the interfering substance in the present embodiment is also installed in the hard disc 401d.

The read-out device 401e is configured by flexible disc drive, CD-ROM drive, DVD-ROM drive, and the like, and is able to read out computer programs and data recorded on a portable recording medium 404. The application program 404a in the present embodiment is stored in the portable recording medium 404, where the computer 401 can read out the application program 404a from the portable recording medium 404, and install the application program 404a in the hard disc 401d.

The application program 404a is not only provided by the portable recording medium 404, but also provided through communication line (wired or wireless) from external devices communicatably connected with the computer 401 by the communication line. For instance, the application program 404a may be stored in the hard disc of the server computer on the Internet, where the computer 401 can access the server computer to download the application program 404a and install the application program 404a in the hard disc 401d.

Operating system providing graphical interface environment such as Windows (registered trademark) manufactured and sold by US Microsoft Co. is installed in the hard disc 401d. In the following description, the application program 404a according to the present embodiment is assumed to be operating on the operating system. The input/output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 transmits and receives data with the detection mechanism unit 2 using a predetermined communication protocol by means of the communication interface 401g. The image output interface 401h is connected to the display section 4b configured by LCD, CRT, or the like, and is configured to output the image signal corresponding to the image data provided from the CPU 401a to the display section 4b. The display section 4b displays the image (screen) according to the input image signal.

The conveying unit 3 has a function of conveying a rack 151 mounted with a plurality of (ten in the present embodiment) test tubes 150 accommodating the sample to the suction position 2a (see FIG. 2) of the measurement device 2. The conveying unit 3 includes a rack set region 3a for setting a rack 151 stored with the test tube 150 accommodating the non-processed sample, and a rack accommodating region 3b for accommodating the rack 151 stored with the test tube 150 accommodating the processed sample.

The measurement device 2 is configured to acquire the optical information on the supplied sample by performing an optical measurement on the sample supplied from the conveying unit 3. In the present embodiment, the optical measurement is performed on the sample dispensed into the cuvette 152 (see FIG. 2) of the measurement device 2 from the test tube 150 mounted on the rack 151 of the conveying unit 3. As shown in FIGS. 1 to 3, the measurement device 2 includes a cuvette supply section 10, a rotation conveying section 20, a sample dispensing arm 30, a HIL detecting section 40, a lamp section 50, two reagent dispensing arms 60, a cuvette transporting section 70, a detecting section 80, an urgent sample setting section 90, a cuvette discarding section 100, a fluid section 110, and a control section 120.

The cuvette supply section 10 is configured to sequentially supply the plurality of cuvettes 152 randomly placed by the user to the rotation conveying section 20. As shown in FIG. 2, the cuvette supply section 10 includes a hopper 12 attached to the apparatus main body by way of a bracket 11 (see FIG. 1); two induction plates 13 attached below the hopper 12; a supporting table 14 arranged on the lower end of the two induction plates 13; and a supply catcher part 15 arranged at a predetermined distance from the supporting table 14. The two induction plates 13 are arranged parallel to each other at a distance smaller than the diameter of the collar part of the cuvette 152 and larger than the diameter of the body part of the cuvette 152. The cuvette 152 supplied into the hopper 12 slidably drops towards the supporting table 14 with the collar part engaged to the upper surface of the two induction plates 13. The supporting table 14 has a function of rotatably transporting the cuvette 152 slidably moved onto the induction plates 13 to a position enabling the supply catcher part 15 to grip the cuvette 152. The supply catcher part 15 is arranged to supply the cuvette 152 rotatably transported by the supporting table 14 to the rotation conveying section 20.

The rotation conveying section 20 is arranged to transport the cuvette 152 supplied from the cuvette supply section 10 and a reagent container (not shown) accommodating the reagent to be added to the sample in the cuvette 152 in the rotating direction. The rotation conveying section 20 is configured by a reagent table 21 of circular form, a reagent table 22 of circular ring form arranged on the outer side of the reagent table 21 of circular form, a secondary dispensing table 23 of circular ring form arranged on the outer side of the reagent table 22 of circular ring form, and a primary dispensing table 24 of circular ring form arranged on the outer side of the secondary dispensing table 23 of circular ring form, as shown in FIG. 2. The primary dispensing table 24, the secondary dispensing table 23, the reagent table 21, and the reagent table 22 respectively rotate in both the clockwise direction and the counterclockwise direction, and are configured to be rotatable independent from each other.

As shown in FIG. 2, the reagent tables 21 and 22 each has a plurality of holes 21a and 22a formed at a predetermined spacing along the circumferential direction. The holes 21a and 22a of the reagent tables 21 and 22 are formed to place the plurality of reagent containers (not shown) accommodating various reagents to be added when preparing a measurement specimen from the sample. The primary dispensing table 24 and the secondary dispensing table 23 each has a plurality of holding parts 24a and 23a arranged at a predetermined spacing in the circumferential direction. The holding parts 24a and 23a are arranged to hold the cuvette 152 supplied form the cuvette supply section 10. In the primary dispensing process, the sample accommodated in the test tube 150 of the conveying unit 3 is dispensed into the cuvette 152 held by the holding part 24a of the primary dispensing table 24. In the secondary dispensing process, the sample accommodated in the cuvette 152 held by the primary dispensing table 24 is dispensed into the cuvette 152 held by the holding part 23a of the secondary dispensing table 23. A pair of small holes is formed in the holding part 24a at positions facing each other at the side of the holding part 24a. The pair of small holes is formed to transmit the light emitted from a branched optical fiber 58 of the lamp unit 50 to be hereinafter described.

The sample dispensing arm 30 has a function of suctioning the sample accommodated in the test tube 150 conveyed to the suction position 2a by the conveying unit 3, and dispensing the suctioned sample into the cuvette 152 transported by the rotation conveying section 20.

The HIL detecting section 40 is configured to acquire the optical information from the sample to measure the presence and the concentration of interfering substances (chyle, hemoglobin, and bilirubin) in the sample before the reagent is added. Specifically, the presence and the concentration of the interfering substance are measured using four types of light (405 nm, 575 nm, 660 nm, and 800 nm) out of the five types of light (340 nm, 405 nm, 575 nm, 660 nm, and 800 nm) irradiated from the lamp unit 50 to be hereinafter described. The light having a wavelength of 405 nm is light that is absorbed by any one of chyle, hemoglobin, and bilirubin. That is, the influence of chyle, hemoglobin, and bilirubin contributes to the optical information measured by the light having the wavelength of 405 nm. The light having a wavelength of 575 nm is light that is not substantially absorbed by bilirubin but is absorbed by chyle and hemoglobin. That is, influence of chyle and hemoglobin contributes to the optical information measured by the light having the wavelength of 575 nm. The light having a wavelength of 660 nm and 800 nm are light that are not substantially absorbed by bilirubin and hemoglobin but are absorbed by chyle. That is, influence of chyle contributes to the optical information measured by the light having the wavelength of 660 nm and 800 nm. The chyle absorbs the light having the wavelength from 405 nm of low wavelength region up to 800 nm of high wavelength region, and the light having the wavelength of 660 nm is more absorbed by the chyle than the light having the wavelength of 800 nm. That is, the influence of the chyle is smaller in the optical information measured by the light having the wavelength of 800 nm than in the optical information measured by the light having the wavelength of 660 nm.

The acquisition of the optical information of the sample by the HIL detecting section 40 is performed prior to the optical measurement (main measurement) of the sample by the detecting section 80. The HIL detecting section 40 acquires optical information from the sample in the cuvette 152 held by the holding part 24a of the primary dispensing table 24, as shown in FIG. 2.

In the present embodiment, the lamp unit 50 is arranged to emit light used in the optical measurement performed in the HIL detecting section 40 and the detecting section 80, as shown in FIG. 2. That is, one lamp unit 50 is configured to be commonly used for the HIL detecting section 40 and the detecting section 80. As shown in FIGS. 1 and 2, the reagent dispensing arm 60 is arranged to mix the reagent into the sample in the cuvette 152 by dispensing the reagent in the reagent container (not shown) mounted on the rotation conveying section 20 into the cuvette 152 held by the rotation conveying section 20. The reagent is thereby added to the sample which optical measurement by the HIL detecting section 40 has terminated, thereby preparing a measurement specimen. The cuvette transporting section 70 is arranged to transport the cuvette 152 between the rotation conveying section 20 and the detecting section 80. A warming pipette 61 configuring a warming device equipped with a warming function of the reagent is attached near the distal end of the reagent dispensing arm 60.

The detecting section 80 has a function of warming the measurement specimen prepared by adding the reagent to the sample, and measuring the optical information from the measurement specimen. As shown in FIG. 2, the detecting section 80 is configured by a cuvette mounting part 81 and a detector 82 arranged below the cuvette mounting part 81.

As shown in FIGS. 1 and 2, the urgent sample setting section 90 is arranged to perform sample analyzing process on the urgent sample. The urgent sample setting section 90 is configured to cut the urgent sample in when the sample analyzing process is being performed on the sample supplied from the conveying unit 3. The cuvette discarding section 100 is arranged to discard the cuvette 152 of the rotation conveying section 20. As shown in FIG. 2, the cuvette discarding section 100 is configured by a discarding catcher part 101, a discarding hole 102 (see FIG. 1) formed at a predetermined distance from the discarding catcher part 101, and a discarding box 103 arranged below the discarding hole 102. The discarding catcher part 101 is arranged to move the cuvette 152 of the rotation conveying section 20 to the discarding box 103 through the discarding hole 102 (see FIG. 1). The fluid section 110 is arranged to supply fluid such as cleaning fluid to the nozzle at each dispensing arm in the shut down process of the sample analyzer 1.

As shown in FIG. 3, the control section 120 is connected to the cuvette supply section 10, the rotation conveying section 20, the sample dispensing arm 30, the HIL detecting section 40, the lamp unit 50, the two reagent dispensing arms 60, the cuvette transporting section 70, the detecting section 80, the urgent sample setting section 90, the cuvette discarding section 100, and the fluid section 110 so as to be able to communicate electric signals. The control section 120 is configured by CPU, ROM, RAM, and the like, and controls the operation of each mechanism described above by having the CPU execute the control program stored in advance in the ROM, whereby the measurement device 2 executes the sample analyzing operation and the maintenance operation (operation for maintenance work), to be hereinafter described.

Process of Sample Analysis

Figure 5:
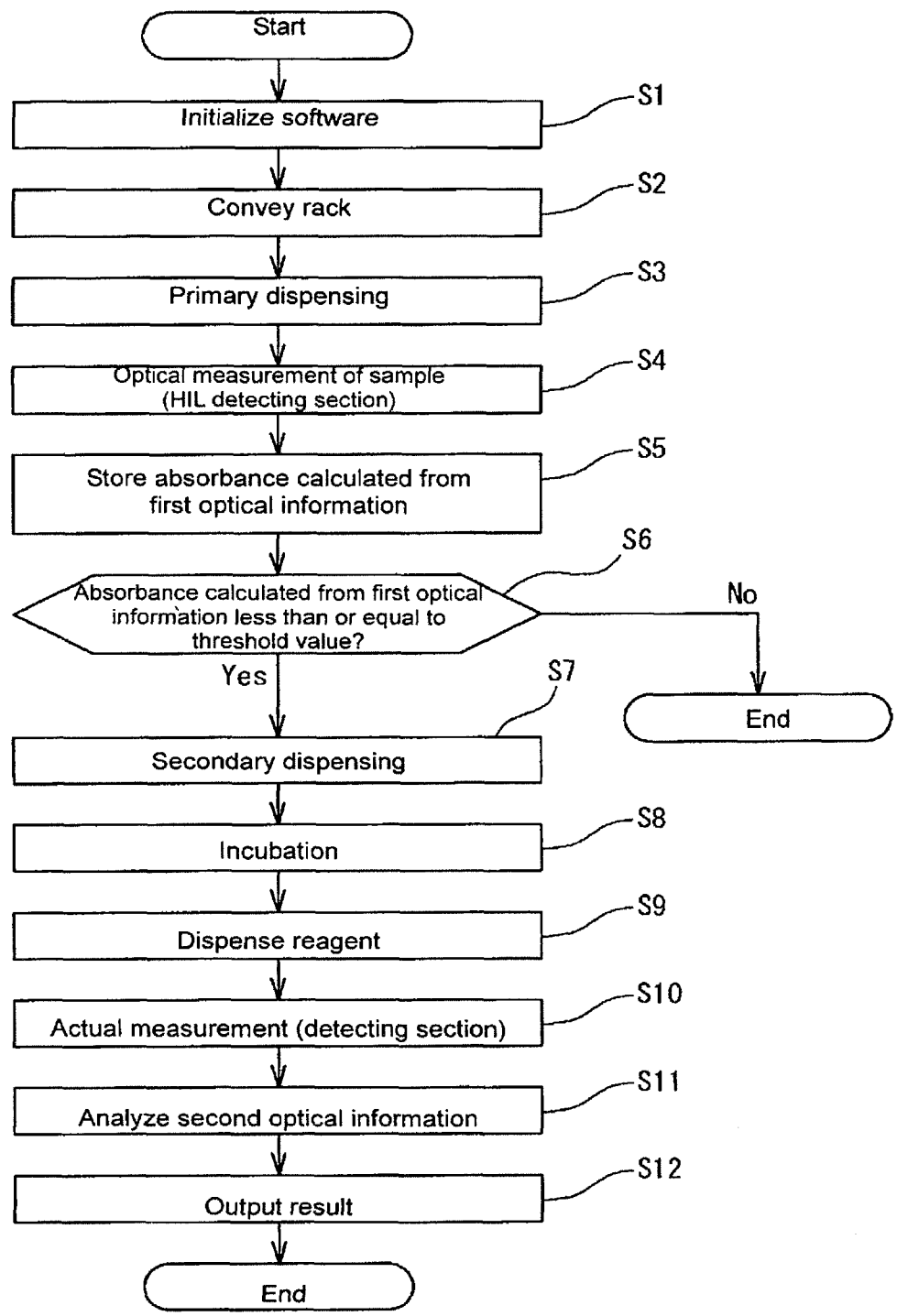
FIG. 5 is a flowchart showing procedures of a sample analyzing operation of the analyzer shown in FIG. 1.

The sample analyzing operation using the analyzer described above will now be briefly described. FIG. 5 is a flowchart showing the procedures of the sample analyzing operation of the analyzer shown in FIG. 1. First, the powers of the measurement device 2 and the control device 4 of the analyzer 1 shown in FIG. 1 are turned ON to carry out the initial setting of the analyzer 1. The operation to return the mechanism moving the cuvette 152 and each dispensing arm to the initial position, and initialization of the software stored in the control section 4a of the control device 4 are performed (step S1).

The rack 151 mounted with the test tube 150 accommodating the sample (blood plasma) is conveyed by the conveying unit 3 shown in FIG. 2. The rack 151 of the rack set region 3a is thereby conveyed to the position corresponding to the suction position 2a of the measurement device 2 (step S2). In step S3, a predetermined amount of sample is suctioned from the test tube 150 by the sample dispensing arm 30. The sample dispensing arm 30 is then moved to above the cuvette 152 held by the primary dispensing table 24 of the rotation conveying section 20. Thereafter, the sample is discharged from the sample dispensing arm 30 into the cuvette 152 of the primary dispensing table 24, and the sample is batched off into the cuvette 152.

The primary dispensing table 24 is then rotated so that the cuvette 152 dispensed with the sample is conveyed to a position where measurement can be performed by the HIL detecting section 40. Thereby, in step S4, optical measurement on the sample is performed by the HIL detecting section 40, and the optical information is acquired from the sample. In step S5, the control section 4a of the control device 4 calculates the absorbance of the sample, and also calculates the presence and the concentration of the interfering substances (chyle, hemoglobin, and bilirubin) in the sample using the data (first optical information) of the received digital signal.

Subsequently, in step S6, whether or not the absorbance stored in the RAM 401c is lower than or equal to a threshold value is determined. If the absorbance calculated from the first optical information measured in the HIL detecting section 40 exceeds the threshold value in step S6, a great amount of interference substance is assumed to be contained in the sample, in which case, an accurate analysis cannot be performed and thus the process is terminated. If the absorbance calculated from the first optical information measured in the HIL detecting section 40 is lower than or equal to the threshold value in step S6, a predetermined amount of sample is suctioned from the cuvette 152 held by the holding part 24a of the primary dispensing table 24 by the sample dispensing arm 30 in step S7. The predetermined amount of sample is then discharged into each of the plurality of cuvettes 152 of the secondary dispensing table 23 from the sample dispensing arm 30 to perform the secondary dispensing process.

In step S8, the quantified sample is incubated for a predetermined time. The incubation time differs depending on the measurement items, but is normally about one to three minutes. The reagent dispensing arm 60 is then driven to add the reagent in the reagent container (not shown) mounted on the reagent tables 21 and 22 into the sample in the cuvette 152 of the secondary dispensing table 23 in step S9. The measurement specimen is thereby prepared. The cuvette 152 of the secondary dispensing table 23 accommodating the measurement specimen is then moved to the insertion hole 81a of the cuvette mounting part 81 of the detecting section 80 using the cuvette transporting section 70.

Thereafter, in step S10, the optical measurement (main measurement) is performed on the measurement specimen in the cuvette 152 by the detector 82 of the detecting section 80 to acquire the optical information (second optical information) from the measurement specimen. After the analysis of step S11 by the control section 4a of the control device 4 is finished, the result of analysis obtained in step S11 is displayed on the display section 4b of the control device 4 in step S12. The sample analyzing operation of the analyzer 1 is terminated in this manner.

Recording and Display of Maintenance History

Various maintenances are performed in order to smoothly operate the analyzer 1 configured as above, and to realize predetermined performances. The maintenance, as mentioned above, includes items manually performed by the user or the service person with the operation of the apparatus in a stopped state such as "sample tube discarding" and "reagent condensation removal", and items that requires the apparatus to be operating such as "pipette cleaning". In the present embodiment, the maintenance record is automatically taken when the latter maintenance operation that involves the operation of the analyzer 1 is implemented. Therefore, the trouble for the user to separately take the maintenance record is eliminated, the load of the user is alleviated, and the maintenance record is automatically taken, whereby forgetting to record or recording mistake is prevented. In the present embodiment, the maintenance history is stored in the RAM 401c (memory section) of the control device 4, and the stored history is displayed on the display section 4b by the instruction of the CPU 401a serving as a display control section. In this case, the maintenance history is displayed on the display section 4b in a calendar form in which the date is displayed in a list, or in a date form depending on the type of items. "Calendar form" is, for example, a form in which the dates of one month are horizontally displayed in a list in one column, where necessity of maintenance implementation are described with signs and characters under the date, and is convenient in displaying the maintenance history for a short term span of every day or every week. "Date form" is a form in which the implementation of the maintenance is written next to, for example, the area where the maintenance item is written in a form of date (indication of Jul. 26, 2006 or Heisei (one of the Japanese calendar systems) 18, July 26), and is convenient in displaying the maintenance history of a long term span of every month or every year.

In the present embodiment, the maintenance history is stored in the apparatus itself with which the user carries out the daily analyzing operation, and the stored maintenance history is displayed on the display section such as display, whereby the operation of the apparatus and the maintenance of the apparatus can be performed in association with each other. Therefore, the maintenance is reliably performed more easily, and analysis of high accuracy can be performed while maintaining the reliability of the apparatus. The maintenance history can be displayed by clicking the icon "maintenance" in the menu screen displayed on the display section 4b when the control device 4 of the analyzer 1 is started up, or clicking the icon "maintenance" in the tool bar.

Figure 6:
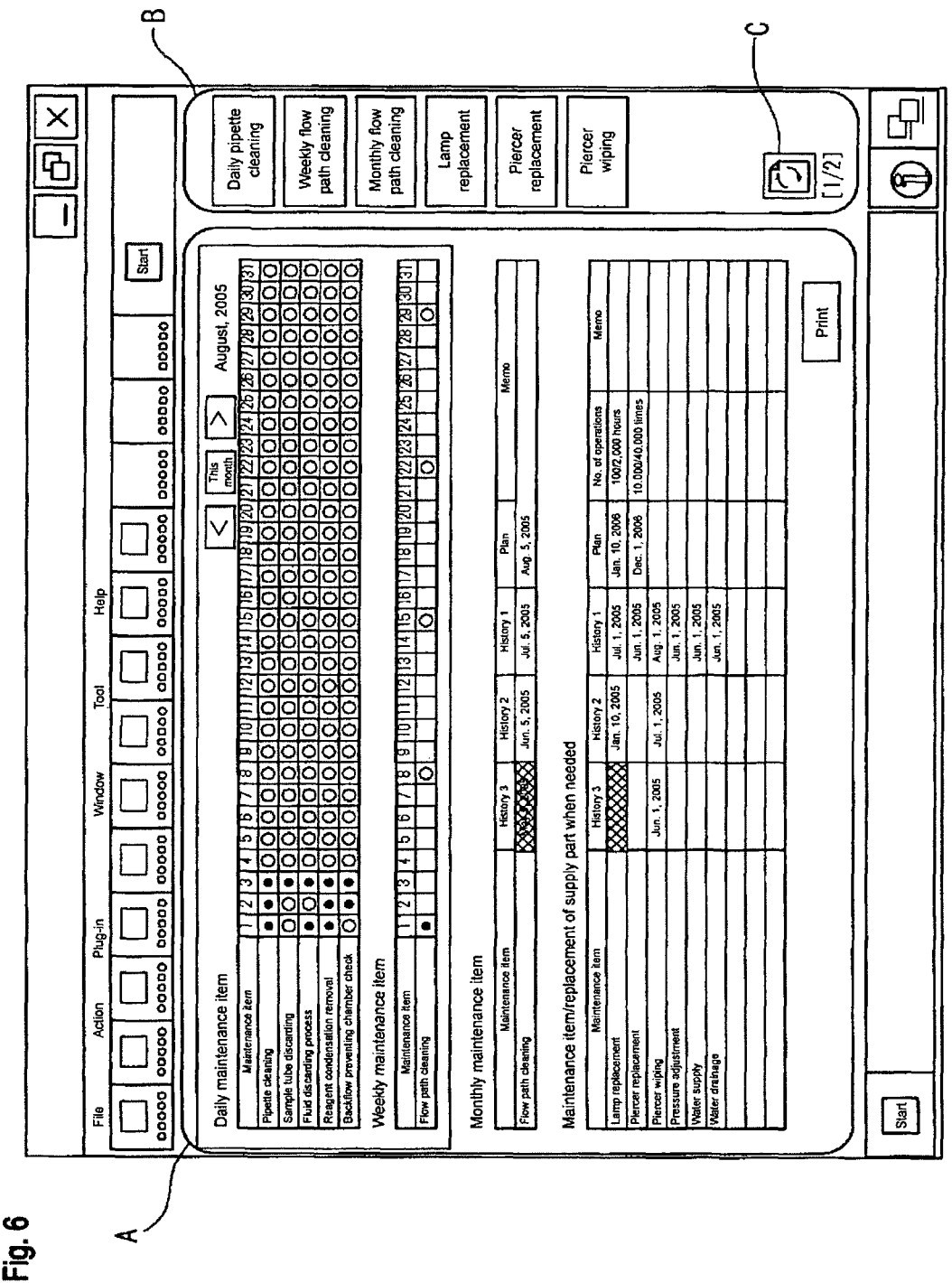
FIG. 6 is a view showing one example of a display screen displayed on the display section.

FIG. 6 is a view showing one example of such display screen. In FIG. 6, A is a maintenance plan/history display region for displaying the maintenance plan and history by the user, and B is an operation panel region for displaying the operation buttons associated with the maintenance screen. Thus, the maintenance operation can be instructed while checking the maintenance history by simultaneously displaying the operation screen for operating the maintenance operation and the history screen for displaying the maintenance history, whereby only the necessary maintenance is reliably implemented.

The maintenance plan/history display region A is divided into four display regions according to the type of maintenance. That is, the maintenance plan/history display region A is divided into "daily maintenance item" normally performed for every apparatus operating day, "weekly maintenance item" performed every week, "monthly maintenance item" performed every month, and "maintenance item/replacement of supply part when required" performed as necessary.

The "daily maintenance item" and the "weekly maintenance item" have the maintenance history recorded in the calendar form as described above. The "daily maintenance item" includes each items of "pipette cleaning" of cleaning the pipette that suctions and dispenses samples and reagents (cleaning in which the extent of cleaning is intensified, and performed separate from the cleaning performed in time of measurement of each sample); "sample tube discarding" of discarding the used cuvette (sample tube) accommodated in the discarding container and emptying the container; "fluid discharging process" of used cleaning fluid and the like; "reagent condensation removal" of removing the condensation attached to the reagent container cooled to about 10° C. to enhance the storage property of the reagent; and "backflow preventing chamber check" of checking with eyes whether fluid is retained in the chamber preventing backflow of the fluid to the compressor, and discarding the fluid if retained. The "weekly maintenance item" includes "flow path cleaning" of cleaning the entire flow path of the fluid such as the tube connected to the pipette.

In the "daily maintenance item", the implementation state mark is displayed in a region (cell) corresponding to each date, where a white circle (○) mark is provided every day to each item in the present embodiment. When the maintenance is implemented, the mark is changed to a black circle (●) mark. In the "weekly maintenance item", ○ is given to a region of every seventh day from the previous implemented date, where "●" mark is given to the cell corresponding to the implemented date when the maintenance is implemented, and the positions of the "○" mark are updated with the relevant implemented date as the reference. The necessary maintenance is reliably implemented by displaying the maintenance plan. That is, the memory section further memorizes the maintenance plan, and the display control section is configured to further display the maintenance plan on the display section. The user is thus able to easily check the maintenance plan in the daily analyzing operation. Therefore, the timing of implementing the maintenance will not be missed, the maintenance task is performed at an appropriate timing, and analysis of high accuracy is performed while maintaining the reliability of the apparatus. In the display of the maintenance history of calendar form, the display control section displays, in correspondence to the date, the first mark "●" indicating that the maintenance task has been implemented if the maintenance task is implemented in the region corresponding to the relevant date, and displays the second mark "○" indicating that the maintenance task has not been implemented if the maintenance task has not been implemented in the relevant region. The user is thus able to easily check visually whether or not the maintenance task has been implemented.

Since the "daily maintenance item" and the "weekly maintenance item" have the maintenance history displayed in calendar form, the maintenance history can be recognized at one view, and the items in which the maintenance has not been implemented can be intuitively recognized. The maintenance thus is reliably implemented. In other words, the maintenance history is displayed on the display section such that date or week is displayed in a list and the implementation state of the maintenance is displayed in correspondence to each date or week, where the display of the maintenance history is updated when the maintenance operation is implemented, and the implemented date of the maintenance task that is frequently implemented (e.g., every day or every week) can be checked at once. The "monthly maintenance item" includes "flow path cleaning", which is the maintenance basically the same as the "flow path cleaning" performed week after week. However, the cleaning sites and the cleaning time differ, and a more thorough cleaning is performed than the cleaning performed week after week.

The "maintenance item/replacement of supply part when required" includes "lamp replacement" of replacing the lamp used as the light source in the measurement unit, "piercer replacement" of replacing the piercer that perforates through a cap when suctioning the sample from the container sealed by the rubber cap, "piercer wiping" of removing dirt from the piercer, "pressure adjustment" of adjusting the pressure of air pressure source (compressor) used in suctioning and dispensing the sample and the like, "water drainage" of draining the water of the flow path inside the apparatus when the apparatus is not used over a long period of time or when changing the installing location of the apparatus, and "water supply" of supplying water into the flow path inside the apparatus. In each item of the "maintenance item/replacement of supply part when required", the maintenance history when required is displayed up to the past three times, and the next implementation planned date and the operation state are displayed. Regarding the components in which the replacement timing can be predicted from the operating time or the number of operating times, the maintenance planned date can be predicted. Such prediction is made by the CPU 401a that functions as a plan date predicting section, where the date can be calculated (predicted) based on the maximum number of operations (time) and the current number of operations (time) of the components as well as the elapsed time from the previous maintenance implemented date. In the present embodiment, the implementation planned dates of lamp replacement and piercer replacement are predicted and displayed. Since the replacement timing of the lamp and the piercer which are consumable goods can be predicted, such consumable goods can be acquired or stocked in advance. Consequently, the operation of the apparatus is prevented from being interrupted due to part shortage, or the like.

The "monthly maintenance item" and the "maintenance item/replacement of supply part when required" are displayed in date form as opposed to the "daily maintenance item" and the "weekly maintenance item" which are displayed in calendar form. In the case of maintenances that are performed on an irregular base such as replacement of consumable goods, the interval of maintenance (replacement task) implementation timing is generally long or in units of month or in units of year, and thus the display becomes small or extends over a plurality of screens and becomes difficult to see if the history thereof is displayed in calendar form, whereas the necessary information can be easily obtained by being displayed in date form. Thus, the display corresponding to the type of maintenance (regular base or irregular base, short term span or long term span) is performed in the present embodiment.

Various operation buttons related to maintenance are displayed in the operation panel region B, where the displayed operation, or preparation or auxiliary operation for the operation, is automatically executed by clicking the relevant button. "Preparation or auxiliary operation for the operation" is, in the case of "pipette replacement", the operation (preparation operation) of moving the pipette to the replacement position and returning the pipette to the original position after the replacement task by hand is completed; and in the case of "lamp replacement", it is the operation (auxiliary operation) of calibrating the lamp after the lamp replacement is performed by hand. That is, "preparation or auxiliary operation for the operation" refers to the operation (operation involved in maintenance task) for the user to perform the maintenance task. In the present embodiment, the maintenance record is automatically made even when such preparation or auxiliary operation is executed assuming that the maintenance related to the operation is executed. In the present specification, the concept of "maintenance operation" not only includes the operation of automatically performing all the steps of the maintenance task as in "flow path cleaning" by the analyzer 1, but also includes the "preparation or auxiliary operation for the operation" described above.

Figure 7:
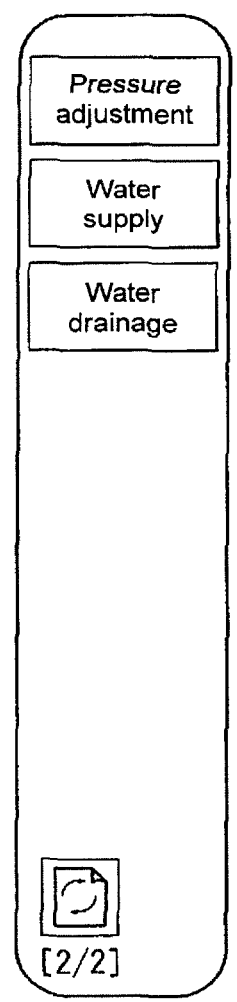
FIG. 7 is a view showing a display example of another page of the operation panel region B in the display screen.

In FIG. 6, C is a display switch button of the operation panel, where the operation panel of the next page is displayed can be clicking the switch button. The "current page/total number of pages" is displayed below the display switch button C. As shown in FIG. 7, each operation button of "pressure adjustment", "water supply", and "water drainage" are displayed in the operation panel of the next page. Among the illustrated operation buttons, a check dialogue (not shown) is displayed with respect to the button associated with "cleaning" when the button is clicked, where cleaning complying with a predetermined sequence starts when "execute" button is clicked in the check dialogue. After "cleaning" is completed, the "●" mark indicating the implementation is completed is automatically given to the cell. In the present embodiment, a configuration of arranging the operation buttons for executing the maintenance operations in the operation panel region B or the operation screen, and having the user make the instruction of the maintenance operation by clicking the corresponding operation button has been described, but other configurations may be adopted as long as it is a means for accepting the instruction of the maintenance operation from the user. For instance, as a means for accepting the instruction of the maintenance operation, a figure (image) different from the button may be displayed in the operation screen as an icon designed, in frame format, of the content of the maintenance operation, and the user may perform the operation of selecting the figure, that is, clicking the mouse or operating the keyboard so that the start instruction of the maintenance operation from the user is accepted. The user thus can give the instruction of the maintenance operation by simply selecting the figure corresponding to the desired maintenance item of the instruction figure displayed in the operation screen.

Figure 8:
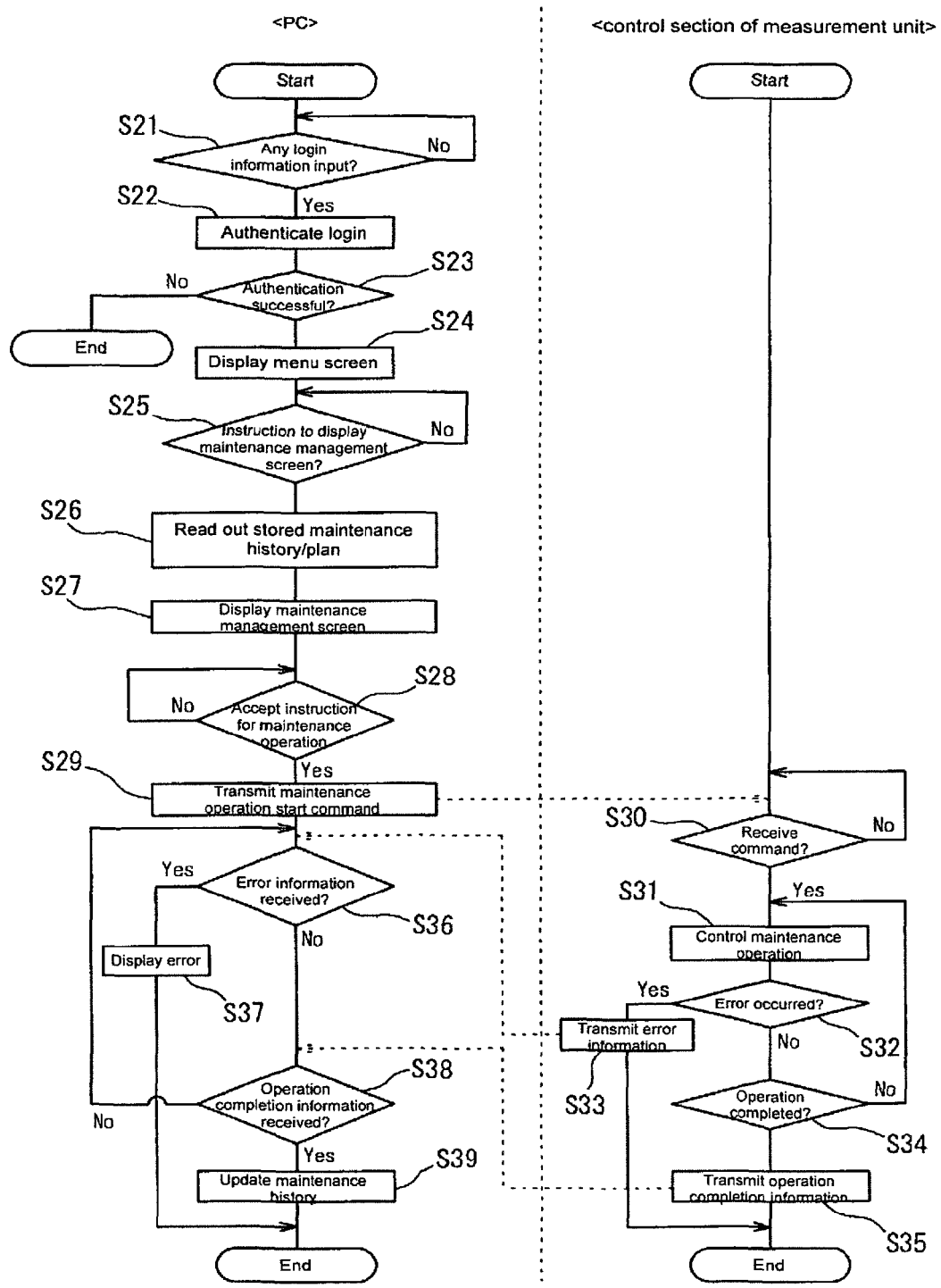
FIG. 8 is a flowchart describing the update of the maintenance history.

The automatic update of the maintenance history associated with the maintenance operation will now be described according to the flowchart of FIG. 8. In the figure, the left half shows the control in the personal computer 401 and the right half shows the control in the control section of the measurement unit.

In step S21, the personal computer (PC) 401 determines whether or not login information such as user name and password is input by the user, and the authentication of the login is performed in step S22 if the predetermined login information is input. In step S23, determination is made on whether or not the authentication is successful, where the operation is terminated if authentication fails, and the menu screen is displayed in subsequent step S24 if authentication is successful. When the user instructs the display of maintenance management screen (e.g., click a predetermined icon) in the menu screen, the maintenance history/plan memorized in the memory means is read (step S26), and the maintenance history/plan is displayed on the maintenance management screen (step S27). In step S28, the personal computer (PC) 401 then determines whether or not the instruction of maintenance operation by the operation of the operation button in the operation panel region B is accepted. If the instruction of maintenance operation is accepted, the personal computer 401 transmits a maintenance operation start command to the control section of the measurement unit in step S29.

In step S30, the control section of the measurement unit determines whether or not the maintenance operation start command is received. If determined that the command is received, the control section of the measurement unit carries out the control such that the corresponding mechanism performs the maintenance operation according to the predetermined sequence in step S31.

In step S32, the control section of the measurement unit determines whether or not error occurred during the maintenance operation, where the error information is transmitted to the personal computer (PC) 401 in step S33 if error occurred. If error did not occur, judgment is made whether or not the predetermined maintenance operation is completed in step S34, where the process returns to step S31 if not completed, and the control of the maintenance operation is continued, and the information of the maintenance operation completion is transmitted to the personal computer (PC) 401 in step S35 if the maintenance operation is completed.

After transmitting the maintenance operation start command to the control section of the measurement unit in step S29, the personal computer (PC) 401 makes a judgment on whether or not the error information is received from the control section of the measurement unit in step S36. If the error information is received, the error display is performed in step S37, and if the error information is not received, judgment is made on whether or not the information of maintenance operation completion is received in step S38. The process returns to step S36 if the information of the maintenance operation completion is not received, and the update of the maintenance history is performed in step S39 if the information of maintenance operation completion is received. Specifically, the maintenance item and date are memorized in the memory section in association with the user name who has logged in, and the "○" mark of the relevant cell in the maintenance management screen is changed to "●" indicating the completion of the implementation.

In the present embodiment, an example of determining whether or not the personal computer (PC) 401 has accepted the instruction of the maintenance operation by the operation of the operation button in the operation panel region B in step S28 has been described, but is not limited thereto, and when the user manually implements the maintenance task that is not dependent on the operation of the operation button, the information on the implementation of the task may be input by hand. In this case, the input of the implementation information of the maintenance task is determined by the personal computer 401, and the processes from step S39 on are executed if determined that there is input.

In the present embodiment, the person in charge of the maintenance may be automatically recorded from the login name. The responsibility system or the management system of the maintenance of the analyzer is thereby clarified. The name of the person in charge is stored in the RAM 401c of the control device 4 that functions as the recording unit. Preferably, the name of the person in charge is not displayed on the display screen for the sake of simplifying the display, and is output only when printing the maintenance history. Thus, since the information on the login user and the maintenance recording are automatically stored in the memory section in association with each other when the maintenance operation of the analyzer is executed, the trouble for the user to separately take the maintenance record is eliminated, and the user who has implemented the maintenance task can be specified by referencing the maintenance record. The management of the information on the maintenance is more appropriately performed by including the person implementing the task in the maintenance record.

There are some maintenance activities, such as "sample tube discarding" and "reagent condensation removal," which can be manually initiated by a user or a service person while the analyzer is not operational. For these manually initiated maintenance activities, the record of maintenance can be entered manually. Hence, the record of manually initiated maintenance activities can be displayed along with the record of other maintenance activities, whereby the overall review of the entire maintenance record become possible. Please note that for the maintenance activities which are initiated by instructions from the personal computer (PC) 401, the user or the service person cannot enter the record of maintenance manually. The mistake is thereby prevented in which a record of maintenance is entered manually for a maintenance activity which has not yet been performed.

Furthermore, the prohibition of manual input can be permitted when the login name defined in advance is input. For instance, when the apparatus is in failure, the maintenance operation by a user can be extraordinarily difficult. In such case, the service person may have the apparatus execute the maintenance. In this case, when the service person inputs the predetermined login name to operate the apparatus, the prohibition of manual input is permitted to allow input manually, so that the maintenance initiated by the service person can be recorded.

The embodiments disclosed herein are illustrative and should not be construed as being restrictive. The scope of the invention is defined by the appended claims rather than by the description of the embodiments, and all changes that fall within meets and bounds of the claims, or equivalence of such meets and bounds are therefore intended to be embraced by the claims.

What is claimed is:

1. A sample analyzer for analyzing a sample, comprising:
   a measurement device that comprises:
      a sample dispensing pipette configured to dispense a sample to a cuvette;
      a reagent dispensing pipette configured to dispense a reagent to the cuvette; and
      a detecting device configured to measure optical information of a measurement sample comprising the sample and the reagent in the cuvette;
   a memory that stores a plan/history of maintenance needed to be performed on the measurement device, wherein the plan/history of maintenance comprises planned dates to perform a maintenance task of cleaning one or more pipette selected from the sample dispensing pipette and the reagent dispensing pipette;
   a display for displaying a maintenance management screen; and
   a controller, comprising a processor and a memory that stores computer programs executable by the processor, which configure the measurement device to:
      (a) display on the display the plan/history of maintenance of the measurement device in a calendar form in the maintenance management screen in such a manner that the maintenance management screen comprises a group of regions associated with the maintenance task of cleaning the one or more pipette, and the regions in the group are associated respectively with a series of dates;
      (b) read out from the plan/history of maintenance stored in the memory, the planned dates to perform the maintenance task of cleaning the one or more pipette and place a not-yet-performed mark in a respective region in the group, corresponding to the read-out planned dates in order to notify the planned dates of the maintenance task of cleaning the one or more pipette;
      (c) receive a request to initiate the maintenance task of cleaning the one or more pipette from a user;
      (d) instruct the measurement device to perform the requested maintenance task of cleaning the one or more pipette;
      (e) receive maintenance completion information from the measurement device;
      (f) automatically update the plan/history of maintenance stored in the memory by automatically recording a date on which the requested maintenance task of cleaning the one or more pipette is performed; and
      (g) after receiving the maintenance completion information, without any involvement of the user, automatically change a not-yet-performed mark displayed in a region, corresponding to the date on which the requested maintenance task of cleaning the one or more pipette is performed, to a different mark indicating that the requested maintenance task of cleaning the one or more pipette has been performed.

2. The sample analyzer according to claim 1, wherein in the process (e), the controller automatically records a login name of the user in addition to the requested maintenance task and the performed date of the requested maintenance task.

3. The sample analyzer according to claim 1, further comprising an input port configured to receive from the user the request to perform the maintenance task of cleaning the one or more pipette.

4. The sample analyzer according to claim 3, further comprising a login section configured to authenticate the user based on user information inputted to the input port, wherein the controller determines whether or not to permit login of the user.

5. The sample analyzer according to claim 1, wherein the series of dates are continuing dates of a calendar month.

6. The sample analyzer according to claim 1, wherein the maintenance tasks are performed on a regular basis.

7. The sample analyzer according to claim 1, wherein the memory stores a program executable by the controller to: in addition to the plan/history of maintenance displayed in the calendar form in the maintenance management screen, display the plan/history of maintenance on the measurement device in a date form in the maintenance management screen in such a manner that the maintenance management screen comprises a group of areas being associated with an additional maintenance task; and read out the planned dates of the additional maintenance task from the plan/history of maintenance stored in the memory and write the read-out planned dates in areas of the group to notify the planned dates of the additional maintenance task.

8. The sample analyzer according to claim 7, wherein the additional maintenance task is performed at irregular intervals.

9. The sample analyzer according to claim 3, wherein the maintenance management screen comprises an operation panel for initiating execution of the maintenance task of cleaning the one or more pipette.

10. The sample analyzer according to claim 9, wherein the operation panel comprises an icon representing the maintenance task of cleaning the one or more pipette, and wherein the input section receives an instruction to execute the maintenance task of cleaning the one or more pipette through an operation by the user of the icon in the operation panel.

11. The sample analyzer according to claim 3, wherein the input port is configured to accept a manual input of a maintenance record from the user, and the controller uses the input of the maintenance record to update the plan/history of maintenance stored in the memory.

12. The sample analyzer according to claim 11, wherein the manual input of the maintenance record is prohibited for a user whose login name is not defined in advance, whereas the manual input is permitted for a user whose login name is defined in advance.

13. A sample analyzer comprising:
a measurement device that comprises a sample dispensing pipette configured to dispense a sample which is a blood or a urine to a cuvette, a reagent dispensing pipette configured to dispense a reagent to the cuvette and a detecting section configured to measure optical information of a measurement sample prepared by the sample and the reagent in the cuvette;
a memory that stores a plan/history of maintenance needed to be performed, wherein the plan/history of maintenance comprises planned dates to perform a maintenance task of cleaning pipettes including the sample dispensing pipette and the reagent dispensing pipette;
a display for displaying a maintenance management screen; and
a controller comprising a processor and a memory that stores computer programs executable by the processor to:
(a) display on the display the plan/history of maintenance in a calendar form in the maintenance management screen in such a manner that the maintenance management screen comprises a group of regions associated with the maintenance task of cleaning the pipettes, and the regions in the group are associated respectively with a series of dates;
(b) from the plan/history of maintenance stored in the memory, read out the planned dates to perform the maintenance task of cleaning the pipettes and place a not-yet-performed mark in a respective region in the group, corresponding to the read-out planned dates in order to notify the planned dates of the maintenance task of cleaning the pipettes;
(c) receive a request to initiate the maintenance task of cleaning the pipettes from a user;
(d) instruct the measurement device to perform the requested maintenance task of cleaning the pipettes;
(e) receive maintenance completion information from the measurement device;
(f) automatically update the plan/history of maintenance stored in the memory by automatically recording a date on which the requested maintenance task of cleaning the pipettes is performed; and
(g) after receiving the maintenance completion information, without any involvement of the user, automatically change a not-yet-performed mark displayed in a region, corresponding to the date on which the requested maintenance task of cleaning the pipettes is performed, to a different mark indicating that the requested maintenance task of cleaning the pipettes has been performed.

14. The sample analyzer according to claim 13, further comprising an input section configured to receive from the user the request to perform the maintenance task of cleaning the pipettes.

15. The sample analyzer according to claim 13, wherein the series of dates are continuing dates of a calendar month.

16. The sample analyzer according to claim 13, wherein the maintenance tasks are performed on a regular basis.

17. The sample analyzer according to claim 13, wherein the memory stores a program executable by the controller to: in addition to the plan/history of maintenance displayed in the calendar form in the maintenance management screen, display the plan/history of maintenance in a date form in the maintenance management screen in such a manner that the maintenance management screen comprises a group of areas being associated with an additional maintenance task; and read out the planned dates of the additional maintenance task from the plan/history of maintenance stored in the memory and write the read-out planned dates in areas of the group to notify the planned dates of the additional maintenance task.

18. The sample analyzer according to claim 17, wherein the additional maintenance task is performed at irregular intervals.

19. The sample analyzer according to claim 14, wherein the maintenance management screen comprises an operation panel for initiating execution of the maintenance task of cleaning the pipettes.

20. The sample analyzer according to claim 19, wherein the operation panel comprises an icon representing the maintenance task of cleaning the pipettes, and wherein the input section receives an instruction to execute the maintenance task of cleaning the pipettes through an operation by the user of the icon in the operation panel.

21. The sample analyzer according to claim 14, wherein the input section is configured to accept a manual input of a maintenance record from the user, and the controller uses the input of the maintenance record to update the plan/history of maintenance stored in the memory.

22. The sample analyzer according to claim 21, wherein the manual input of the maintenance record is prohibited for a user whose login name is not defined in advance, whereas the manual input is permitted for a user whose login name is defined in advance.

* * * * *